United States Patent [19]

Coste et al.

[11] Patent Number: 5,026,900

[45] Date of Patent: Jun. 25, 1991

[54] PROCESS FOR THE PREPARATION OF DIALKYL MALONATES

[75] Inventors: Philippe Coste, Villeurbanne; Philippe Leconte, Lyon; Robert Perron, Charly; Michel Baudoin, Craponne, all of France

[73] Assignee: Rhone-Poulenc, Courbevoie Cedex, France

[21] Appl. No.: 353,612

[22] Filed: May 18, 1989

[30] Foreign Application Priority Data

May 19, 1988 [FR] France ................................. 88 06732

[51] Int. Cl.$^5$ .......................... C07C 67/36; B01J 38/68
[52] U.S. Cl. ..................................... 560/204; 502/24; 560/190; 560/193; 562/590
[58] Field of Search ....................... 560/190, 193, 204; 502/24; 562/590

[56] References Cited

U.S. PATENT DOCUMENTS

| | | | |
|---|---|---|---|
| 3,116,306 | 12/1963 | Heck et al. ...................... | 260/410.9 |
| 4,399,300 | 8/1983 | Prange et al. ...................... | 560/204 |
| 4,508,917 | 4/1985 | Jenck .................................. | 560/204 |
| 4,539,423 | 9/1985 | Statani et al. ...................... | 560/204 |
| 4,570,016 | 2/1986 | Bruner et al. ...................... | 560/204 |
| 4,578,367 | 3/1986 | Hofmann ............................. | 502/24 |
| 4,645,855 | 2/1987 | Reuvers et al. ..................... | 560/204 |

FOREIGN PATENT DOCUMENTS 2313345 12/1976 France .
1448646 9/1976 United Kingdom .

Primary Examiner—Michael L. Shippen
Assistant Examiner—Vera C. Clarke
Attorney, Agent, or Firm—Finnegan, Henderson, Farabow, Garrett, and Dunner

[57] ABSTRACT

A process for the preparation of alkyl malonates by carbonylation of chloroacetate in the presence of a carbonyl source, a carbonylation catalyst, such as chromium carbonyl and an aliphatic alcohol, this reaction being carried out in a two-phase liquid medium.

A process for recycling the catalyst also forms part of the invention.

26 Claims, No Drawings

PROCESS FOR THE PREPARATION OF DIALKYL MALONATES

BACKGROUND OF THE INVENTION

The present invention relates to a process for the preparation of dialkyl malonates. The terms malonates and alkyl malonates as used herein refer specifically to dialkyl malonates.

Dialkyl malonates are compounds employed as a synthesis intermediate in the preparation of many plant-protection and pharmaceutical compounds.

It is known to prepare dialkyl malonates, for example, according to the article described in Ullmann, 1960, vol. 12, p. 192, by condensing the sodium salt of monochloroacetic acid with sodium cyanide in water, followed by esterification with ethanol.

This process enables malonates to be manufactured only at a high cost and under safety conditions which are difficult to maintain. Accordingly, companies which manufacture malonates have for some years endeavored to improve the methods of preparation of malonates, especially from less costly raw materials, such as carbon monoxide.

The first process for the synthesis of malonates from ethyl chloroacetate and carbon monoxide was described in U.S. Pat. No. 3,116,306, in which a carbonylation of an alkyl halide is carried out in the presence of a cobalt tetracarbonyl salt of formula $Co(CO)_4M$ in which M denotes an alkali or alkaline-earth metal, zinc, mercury, tin or iron in the presence of an organic base such as tertiary amines or sodium and potassium alcoholates. It is stated in this text that alkali metal hydroxides may be employed, but that they react with the alkyl halide to form undesirable byproducts.

Some processes based on the above-mentioned process have been described, for example in Patent No. FR 2,253,006, where the carbonylation catalyst is cobalt carbonyl instead of the salt described in U.S. Pat. No. 3,116,306.

Patent No. FR 2,313,345 also describes a process for the preparation of malonates from chloroacetate in the presence of carbon monoxide and a catalyst containing cobalt, the reaction being carried out in a homogeneous medium and in the presence of a solution of sodium hydroxide in an alcohol. During the reaction the use of an alcoholic solution of an alkali metal hydroxide produces one mole of water per mole of chloroacetate consumed; however, in a reaction of this kind, water is normally avoided because it causes the hydrolysis of the ester groups with subsequent formation of a monoalkyl malonic acid or of an acetic ester, which greatly reduces the reaction yield. Separation of the sodium chloride formed and recycling of the catalyst are difficult.

Several patents (U.S. Pat No. 4,399,300 and GB No. 1,448,646) also describe the use of an organic base in an anhydrous medium to avoid the ester saponification phenomena. Sodium ethylate is one such organic base. The disadvantage of employing this base is primarily its cost; furthermore, the use of large quantities of ethylate destroys the malonate and the chloroacetate. As in the preceding patent, at the end of the reaction there is a precipitation of sodium chloride, which is difficult to separate from the malonate.

The present invention has made it possible to solve the problems present in the prior art. The invention makes it possible to produce dialkyl malonates from an alkyl chloroacetate under satisfactory safety conditions and at a lower cost than in the processes of the prior art; it also permits an easy separation of the salts formed and the malonate, and easy recycling of the catalyst.

The process of the present invention can prepare dialkyl malonates by carbonylation of alkyl chloroacetate in the presence of an aliphatic alcohol, a carbonyl source such as carbon monoxide and a catalyst, wherein the reaction takes place in a two-phase liquid medium.

It was not obvious to perform this reaction in a two-phase medium containing water since it was known from the prior art that the presence of water causes the hydrolysis of esters. By performing the reaction of the present invention in a two-phase medium, it is advantageously possible to employ bases which are much less costly, such as alkali metal hydroxides, and, in addition, it permits an easy separation of the salts formed during the carbonylation reaction.

The malonates prepared by the process of the present invention are preferably alkyl malonates whose alkyl chain contains one to four carbon atoms and more preferably are diethyl malonate.

The reaction of carbonylation of alkyl chloroactates may be outlined as follows.

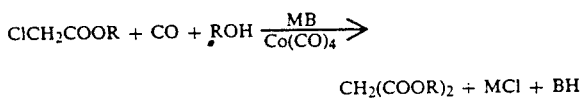

$$CH_2(COOR)_2 + MCl + BH$$

The aliphatic alcohol is preferably chosen from alcohols whose alkyl chain contains one to four carbon atoms; the use of ethyl alcohol is preferred.

The catalyst for the carbonylation reaction is preferably a cobalt-based catalyst; the use of a cobalt tetracarbonyl salt is preferred.

Use of a base in the reaction of the present invention is preferred. The base (MB) is preferably chosen from organic or inorganic bases such as:
  sodium ethyl malonate
  sodium phosphates
  sodium acetate; and
  alkali metal hydroxides.

The use of alkali metal hydroxides is most preferred.

The two-phase liquid medium consists of an aqueous phase serving as a medium for dissolving the inorganic base and of a hydrophobic organic phase. This organic phase is preferably chosen from:
aromatic solvents such as:
  toluene
  xylenes
aliphatic solvents such as:
  alkanes
  cyclohexane
ethers such as:
  diisopropyl ether
  methyl tert-butyl ether
ketones such as:
  methyl isobutyl ketone
esters such as:
  alkyl chloroacetate
  ethyl acetate
  dialkyl malonate.

It is preferable to employ molar ratios of alcohol to the reactant alkyl chloroacetate ranging from 0.1:1 to 10:1, and still more preferably an approximately stoichiometric ratio. A ratio outside these limits is not ruled out of the invention, but does not contribute any particular advantage.

The concentrations of the various reactants in the organic phase preferably range from 0.1 mole to 10 moles per liter in the case of the chloroacetate, which makes it possible to work in pure alkyl chloroacetate. The cobalt-based catalyst is preferably employed at a concentration ranging from $10^{-5}$ mole to 0.1 mole per liter in the organic phase. The quantity of water employed must be sufficient to obtain a two-phase medium; a volume ratio of at least 0.05:1, calculated relative to the organic solvent, is preferred.

A base, if used, may be employed according to the stoichiometry of the reaction to neutralize the hydrochloric acid formed.

When an alkali metal hydroxide is employed as a base, it is preferable to inject it continuously at a controlled pH which may be between 3 and 8 and still more preferably at a pH of approximately 5. This pH may be controlled by the addition of a basic buffer, for example, phosphate.

When a base other than an alkali metal hydroxide is employed, it may be introduced equally well at the beginning of the reaction or continuously.

The carbon monoxide may be introduced in a pure form or mixed with inert gases, such as nitrogen, carbon dioxide or hydrogen, in a quantity of less than or equal to 20% by volume. However, no marked advantage is contributed by this addition of inert gases.

The reaction pressure preferably ranges from 1 to 300 bar and more preferably ranges from 5 to 20 bar; the reaction temperature preferably ranges from ambient temperature to 150° C. and more preferably from 50 to 100° C.

At the end of the reaction, the reaction medium is preferably neutralized to a pH less than or equal to 7, and the inorganic chlorides and the carboxylic acid salts in the aqueous phase are separated off by decanting. The carboxylic acid salts can be recycled for a new esterification.

The cobalt tetracarbonyl salt catalyst is always in the organic phase with the alkyl malonate. To make the process economical the catalyst must be extracted from this organic medium, so that it can be recycled for a new operation. This recycling, which also forms part of the invention, is performed in four steps.

The first step of catalyst recycling consists of extracting the catalyst from the organic phase by oxidation. The resulting cobalt(II) salt is soluble in an aqueous medium. This oxidation of the cobalt is easily performed using a strong acid, for example a halogenated acid, according to the reaction:

$$MCo(CO)_4 + 3H^+ \rightarrow Co^{++} + 4CO + M^+ + 3/2H_2.$$

This reaction is preferably carried out in the presence of alkyl chloroacetate according to the reaction

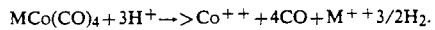
$$3ClCH_2COOEt + Co^-(CO)_4 + 3H^+ \rightarrow 2Co^{++} + 8CO + 3Cl^- + 3CH_3COOEt.$$

After extraction of the catalyst, the organic phase contains the organic substances chloroacetate and malonate, which are separated by any method known to a person skilled in the art, including distillation.

The second step of the process for recycling the cobalt consists of extracting the cobalt in its oxidation state (+2) from the aqueous phase using a heavy acid (AH) preferably containing 6 to 20 carbon atoms. The cobalt is converted into a cobalt dicarboxylate ($CoA_2$) in the presence of an alkaline inorganic base according to the following reaction.

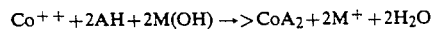
$$Co^{++} + 2AH + 2M(OH) \rightarrow CoA_2 + 2M^+ + 2H_2O$$

in which:
  AH denotes the heavy acid,
  M(OH) denotes the inorganic base
in which:
  M is an alkali metal cation.

The cobalt dicarboxylate is extracted from the aqueous phase with an organic solvent chosen from aromatic derivatives such as:
  xylenes,
  toluene,
ketones such as:
  methyl isobutyl ketone (MIBK),
  acetophenone,
  diisopropyl ketone,
  methyl isopropyl ketone,
  dibutyl ketone,
ethers such as:
  isopropyl ether,
  diphenyl ether,
  methyl isobutyl ether,
alkanes such as:
  cyclohexane,
  methylcyclohexane,
alcohols containing at least 3 carbon atoms, such as:
  isopropanol,
  butanol,
and esters such as:
  ethyl acetate,
  alkyl benzoate.

A solvent corresponding to that employed during the carbonylation is preferably employed.

As stated above, the heavy acid allowing the cobalt to be extracted is preferably chosen from carboxylic acids containing 6 to 20 carbon atoms.

Among these acids may be mentioned:
  oleic acids,
  palmitic acids,
  stearic acids,
  2ethylhexanoic acid.

The use of 2-ethylhexanoic acid is very particularly preferred.

The third step of the cobalt recycling process consists in reducing the cobalt from its oxidation state (+2) to the oxidation state (0) with a mixture of hydrogen and carbon monoxide according to the reaction:

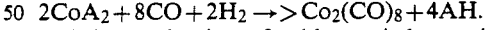
$$2CoA_2 + 8CO + 2H_2 \rightarrow Co_2(CO)_8 + 4AH.$$

This reaction is preferably carried out with the aid of a carbon monoxide-hydrogen mixture preferably containing a $CO/H_2$ molar ratio in the range of 0.1:1 to 10:1 and in the presence of $Co^0$ initiator, for example, $Co_2(CO)_8$ originating from a preceding operation, in a quantity ranging from 0.1 to 10 mol % relative to $Co^{++}$.

Insofar as the operating conditions in particular are concerned, the reduction is preferably carried out at a temperature ranging from the ambient temperature to 150° C. The reaction pressure preferably ranges from 1 to 300 bar.

The cobalt octacarbonyl or the cobalt in the oxidation state (0) in solution in an organic solvent is disproportionated in a fourth step into a tetracarbonylcobaltate (−I) and a salt of cobalt in the oxidation state (+2) by addition of an inorganic base, preferably alkaline and more preferably sodium hydroxide, according to the reaction:

$$2AH + 3/2 Co_2(CO)_8 + 2M(OH) \rightarrow 2MCo(CO)_4 + CoA_2 + 2H_2O + 4CO.$$

The tetracarbonylcobaltate (−I) salt, the carbonylation catalyst, is easily separable in the aqueous phase of the medium by decanting, and it is then introduced into the presence of the compounds to be carbonylated for a new carbonylation to be carried out in a two-phase liquid medium.

The present invention will be described more completely with the aid of the following example, which should not be considered as limiting the invention.

EXAMPLE 100-1 reactor made of Hastelloy B-2 ®
5.6 kg of a 28% solution of $H_3PO_4$
14.16 kg of ethanol
19.9 kg of toluene.

The pH is adjusted to 7 using sodium hydroxide. After making inert 3 times with 5 bar of nitrogen followed by 3 times 5 bar of CO, 6 kg of a solution of $NaCo(CO)_4$ catalyst are then introduced [3.5 mol of $Co^{-1}$].

The reactor is heated to 70° under 10 bar of CO, and 30 kg of ethyl chloroacetate are then introduced at a constant rate over 2 h 15 min. During the reaction the pH of the reaction mixture is kept at 5.3 by addition of 30% NaOH. As soon as the introduction of ethyl chloroacetate is finished, the reaction mixture is cooled to 40° C. under 10 bar of CO, and is then adjusted to pH 7 by addition of 30% NaOH. After release of gaseous CO to atmospheric pressure, the mixture is separated into two phases.

The organic phase is treated in a 160-1 reactor with a 38% solution of HCl until the release of CO is no longer detected by on-line analysis (pH=3.8-4).

An aqueous phase containing $CoCl_2$ and a colorless organic phase containing 31.5 kg of diethyl malonate are obtained, that is a malonate/chloroacetate yield=90.5%.

1,908 g of $CoCl_2$ solution (3.5% of Co) originating from the preceding $Co^{-1}$ oxidation step are mixed with a solution of 2-ethylhexanoic acid in toluene (554 g–302 g).

A 30% solution of NaOH is run into this mixture until the pH is 6. At the end of the pouring, 944.9 g of violet organic phase containing 6.7% of cobalt are separated off. The residual aqueous phase (2,136 g) contains 2,000 ppm of cobalt.

The organic phase of cobalt 2-ethylhexanoate obtained previously is introduced into a stainless steel reactor. The mixture is purged three times under 5 bar of nitrogen and then with CO. 0.01 mol of $Co_2(CO)_8$ is then added to the above mixture, which is then allowed to react for 2 hours at 90° C. under a $CO/H_2$ pressure=20 bar ($CO/H_2$ 4/1).

After cooling to 50° C., the $Co_2(CO)_8$ is determined using iodine.

The $Co^0/Co^{++}$ yield is 80%.

The $Co_2(CO)_8$ solution is treated at 80° C. with 580 g of a normal solution of NaOH under 10 bar of CO. The reaction is allowed to proceed while degassing continuously until the reactor pressure becomes constant at P=3 bar.

After cooling, 700 g of aqueous solution of $NaCo(CO)_4$ are isolated in water at a concentration of 0.90 mol/kg. This solution can be employed in the carbonylation of ethyl chloroacetate to diethyl malonate.

The final organic phase is recycled to the $CoCl_2$ extraction.

What is claimed is:

1. A process for the preparation of a dialkyl malonate comprising the step of carbonylation of an alkyl chloroacetate in the presence of an aliphatic alcohol, a carbon monoxide and a carbonylation catalyst, wherein the carbonylation is carried out in a two-phase liquid medium.

2. The process as claimed in claim 1 wherein said catalyst is a cobalt tetracarbonyl salt.

3. The process of claim 1, wherein said catalyst is a cobalt carbonyl complex.

4. The process of claim 1, wherein the carbonylation is carried out in a two-phase liquid medium comprising water and an aprotic solvent.

5. The process of claim 1, wherein said solvent is selected from the group consisting of toluene, methyl isobutyl ketone, ethyl acetate, xylene, cyclohexane and its derivatives, an ether, an alkyl chloroacetate and an alkyl malonate.

6. The process of claim 4, wherein the molar ratio of alcohol to solvent is from 0.1:1 to 10:1.

7. The process of claim 6, wherein said alcohol and solvent are in stoichiometric ratio.

8. The process of claim 2, wherein the carbonylation is carried out in solvents comprising water and toluene.

9. The process of claim 1, wherein the carbonylation is carried out in a two-phase liquid medium comprising at least one base selected from sodium ethyl malonate, sodium phosphates, sodium acetate and alkali metal hydroxides.

10. The process of claim 9, wherein the base is an alkali metal hydroxide.

11. The process of claim 1, wherein the aliphatic alcohol contains 1 to 4 carbon atoms.

12. The process of claim 1, wherein the aliphatic alcohol is ethyl alcohol.

13. The process of claim 1, wherein the pH is maintained from 3 to 8 during the reaction by continuous addition of aqueous sodium hydroxide.

14. The process of claim 1, wherein the carbonylation is carried out at a temperature ranging from ambient to 150° C.

15. The process of claim 14, wherein the carbonylation is carried out at a temperature ranging from 50° to 100° C.

16. The process of claim 1, wherein the carbonylation is carried out under a pressure ranging from 1 to 300 bar.

17. The process of claim 16, wherein the carbonylation is carried out under a pressure ranging from 5 to 20 bar.

18. A process for recycling a cobalt carbonyl complex employed during a carbonylation carried out in a two-phase liquid medium, comprising the steps of
(1) oxidizing the cobalt to oxidation state (+2) by addition of a strong acid,
(2) extracting the oxidized cobalt (Co II) by converting the oxidized cobalt to cobalt dicarboxylate by utilizing a carboxylic acid effective for said converting in the presence of an alkaline inorganic base and extracting the cobalt dicarboxylate by utilizing an organic solvent;

(3) reducing the cobalt carboxylate with a mixture of hydrogen and carbon monoxide in the presence of a $Co^0$ initiator to form cobalt octacarbonyl; and (4) disproportionating the reduced cobalt by addition of an inorganic base and separating the resulting tetracarbonylcobaltate.

19. The process of claim 18, wherein the oxidation in the first step is carried out using hydrochloric acid.

20. The process of claim 18, wherein the carboxylic acid in the second step is 2-ethylhexanoic acid.

21. The process of claim 18, wherein the organic solvent in the second step is selected from the group consisting of xylene, toluene, an ester, a ketone, an aliphatic or an aromatic ether and an alkane.

22. The process of claim 21, wherein the solvent is toluene.

23. The process of claim 18, wherein the reduction in the third step is carried out with a carbon monoxide-hydrogen mixture containing a hydrogen/carbon monoxide molar ratio ranging from 0.1:1 to 10:1.

24. The process of claim 23, wherein the reduction is carried out at a temperature ranging from ambient temperature to 150° C.

25. The process of claim 23, wherein the reduction is carried out at pressure ranging from 1 to 300 bar.

26. The process of claim 18, wherein the disproprotionation is carried out by the addition of an aqueous solution of sodium hydroxide.

* * * * *

UNITED STATES PATENT AND TRADEMARK OFFICE
CERTIFICATE OF CORRECTION

PATENT NO. : 5,026,900

DATED : June 25, 1991

INVENTOR(S) : Philippe Coste et al

It is certified that error appears in the above-identified patent and that said Letters Patent is hereby corrected as shown below:

Title Page:

Item [73] Assignee, change "Rhone-Poulenc" to --Rhone-Poulenc Chimie--.

Claim 2, column 6, line 12, after "1" insert --,--.

Claim 8, column 6, line 29, change "2" to --1--.

Claim 12, column 6, line 40, change "1" to --11--.

Claim 25, column 8, line 11, after "at" insert --a--.

Claim 26, column 8, lines 12 and 13, change "disprotionation" to --disproportionation--.

Signed and Sealed this

Thirteenth Day of April, 1993

*Attest:*

STEPHEN G. KUNIN

*Attesting Officer*     *Acting Commissioner of Patents and Trademarks*